US010449286B2

(12) United States Patent
Cho

(10) Patent No.: US 10,449,286 B2
(45) Date of Patent: Oct. 22, 2019

(54) FEMORAL ARTERIAL CANNULA CAPABLE OF GUIDING BIDIRECTIONAL PERFUSION FLOW

(71) Applicant: Samsung Life Public Welfare Foundation, Seoul (KR)

(72) Inventor: Yang Hyun Cho, Seoul (KR)

(73) Assignee: Samsung Life Public Welfare Foundation, Seoul (KR)

(*) Notice: Subject to any disclaimer, the term of this patent is extended or adjusted under 35 U.S.C. 154(b) by 0 days.

(21) Appl. No.: 15/551,613

(22) PCT Filed: Feb. 24, 2016

(86) PCT No.: PCT/KR2016/001772
§ 371 (c)(1),
(2) Date: Aug. 17, 2017

(87) PCT Pub. No.: WO2016/137212
PCT Pub. Date: Sep. 1, 2016

(65) Prior Publication Data
US 2018/0043085 A1    Feb. 15, 2018

(30) Foreign Application Priority Data
Feb. 24, 2015 (KR) .................. 10-2015-0026099

(51) Int. Cl.
*A61M 1/36* (2006.01)
*A61M 25/00* (2006.01)
*A61M 1/10* (2006.01)

(52) U.S. Cl.
CPC ........ *A61M 1/3659* (2014.02); *A61M 1/1008* (2014.02); *A61M 25/007* (2013.01);
(Continued)

(58) Field of Classification Search
CPC ............ A61M 1/3659; A61M 25/0043; A61M 25/007; A61M 25/0041; A61M 1/1008; A61M 2025/0008
See application file for complete search history.

(56) References Cited

U.S. PATENT DOCUMENTS 5,171,218 A    12/1992  Fonger et al.
5,425,724 A *  6/1995  Akins ................... A61M 25/06
                                                          600/585
(Continued)

FOREIGN PATENT DOCUMENTS

KR    10-2014-0068069 A    6/2014
WO    WO 2013/025727 A1    2/2013

OTHER PUBLICATIONS

International Search Report and Written Opinion issued by the Korean Intellectual Property Office, acting as the ISA, for International Application PCT/KR2016/001772 dated May 26, 2016.

*Primary Examiner* — Theodore J Stigell
(74) *Attorney, Agent, or Firm* — McCarter & English, LLP

(57) ABSTRACT

The present invention relates to a cannula for femoral arterial bidirectional (a heart direction and a distal lower extremity direction) perfusion. The cannula, which has a cannula tube to be inserted into a blood vessel of the femoral artery, includes a perfusion guide channel formed as a concave part from a predetermined portion of an inner circumferential surface at an end of the cannula tube to the opposite end thereof in a length direction and further includes a through-hole provided at a boundary portion between the perfusion guide channel and the cannula tube in an end direction of the cannula tube, or includes a through-hole provided in a predetermined portion of an inner circumferential surface of an end of the cannula tube and a guide cover provided at an upper portion of the through-hole to cover the upper portion of the through-hole and guide perfusion. During surgery, perfusion proceeds towards the distal limb and thus blood may be stably supplied, and thus ischemia prevalence of the distal limb may be significantly reduced. Accordingly, the cannula can replace conventional techniques used for distal limb perfusion and may stably (Continued)

perform femoral arterial cannulation without technical difficulties such as complications or breakage of blood vessels.

6 Claims, 3 Drawing Sheets

(52) U.S. Cl.
CPC .... *A61M 25/0041* (2013.01); *A61M 25/0043* (2013.01); *A61M 2025/0008* (2013.01)

(56) References Cited

U.S. PATENT DOCUMENTS

| | | | | |
|---|---|---|---|---|
| 5,569,182 | A * | 10/1996 | Twardowski | A61M 5/1582 604/264 |
| 5,800,408 | A | 9/1998 | Strauss et al. | |
| 5,928,192 | A * | 7/1999 | Maahs | A61B 17/12036 604/96.01 |
| 5,976,114 | A * | 11/1999 | Jonkman | A61M 25/001 604/264 |
| 6,042,576 | A * | 3/2000 | DeVries | A61M 25/007 604/264 |
| 6,099,506 | A | 8/2000 | Macoviak et al. | |
| 6,186,981 | B1 * | 2/2001 | Cho | A61M 25/0043 604/117 |
| 6,626,872 | B1 * | 9/2003 | Navia | A61B 17/11 604/264 |
| 8,535,294 | B2 * | 9/2013 | Fischell | A61M 25/0054 604/524 |
| 8,764,819 | B2 * | 7/2014 | Taub | A61B 17/12036 600/16 |
| 8,795,253 | B2 | 8/2014 | Moshinsky et al. | |
| 9,220,872 | B2 * | 12/2015 | Ravikumar | A61B 17/3415 |
| 9,981,119 | B2 * | 5/2018 | Walther | A61M 39/22 |
| 2017/0049997 | A1 * | 2/2017 | Chao | A61M 25/0075 |

* cited by examiner

FEMORAL ARTERIAL CANNULA CAPABLE OF GUIDING BIDIRECTIONAL PERFUSION FLOW

CROSS-REFERENCE TO RELATED APPLICATIONS

This application is the National Stage entry under 35 U.S.C. § 371 of International Application Number PCT/KR2016/001772 filed on Feb. 24, 2016, published on Sep. 1, 2016 under publication number WO 2016/137212 A1, which claims the benefit of priority under 35 U.S.C. § 119 of Korean patent application number 10-2015-0026099 filed Feb. 24, 2015.

TECHNICAL FIELD

The present invention relates to a cannula for guiding perfusion in a direction into which a femoral arterial cannula is inserted and in a direction opposite to the insertion direction, and more particularly, to a femoral arterial cannula capable of guiding bidirectional perfusion that is provided, at an inner circumferential surface of an end of a cannula tube of a cannula to be inserted into the femoral artery, with a perfusion guide channel or a through-hole together with the perfusion guide channel, or with a through-hole that is larger than the through-hole and a guide cover to cover an upper portion of the through-hole so that perfusion flows even in a distal direction of the lower extremity from the femoral artery via the perfusion guide channel, the perfusion guide channel and the through-hole, or the through-hole and the guide cover.

BACKGROUND ART

Extracorporeal circulation is used as heart adjuvant therapy for heart surgery of patients, or in a state of heart failure, and femoral arterial cannulation is commonly used to supply oxygenated blood. Such femoral arterial cannulation is carried out by surgically exposing blood vessels, but, in many cases, a Seldinger's technique whereby a guidewire is inserted via the skin is used. At this time, a cannula is inserted into the femoral artery in the vicinity of the groin region, and thus the biggest problem is distal limb perfusion. In femoral arterial cannulation, blood is supplied to the upper body part above the thigh of a patient, but distal perfusion decreases or is blocked by a thick cannula. Thus, while a femoral arterial cannula is maintained, blood is not supplied from the legs below the thigh to a distal portion, i.e., the feet, and, accordingly, there may be a risk for necrosis of the legs.

Thus, to prevent the occurrence of these problems, various techniques, such as separate antegrade catheterization, posterior tibial artery cannulation, and the like which supply blood to sides of the legs, are conventionally used, but all the techniques cause complications or breakage of blood vessels, and thus there are technical difficulties in applying these techniques.

DETAILED DESCRIPTION OF THE INVENTION

Technical Problem

To address the problems described above, the present invention provides a femoral arterial cannula capable of guiding bidirectional perfusion that is provided, at an end thereof, with a perfusion guide channel or a through-hole together with the perfusion guide channel so that, during surgery, blood is supplied to the heart or the lung, and a part of the blood supplied to the heart or the lung inversely flows via the perfusion guide channel or the through-hole and the perfusion guide channel, thereby supplying blood even to the distal limb on the opposite side.

Another object of the present invention is to provide a femoral arterial cannula capable of guiding bidirectional perfusion, provided with a through-hole and a guide cover protruding therefrom to cover the though-hole at an end thereof so that a part of extracorporeally circulated blood inversely flows via the through-hole and the guide cover to thereby supply blood even to the distal limb on the opposite side.

Technical Solution

According to an aspect of an embodiment, a femoral arterial cannula capable of guiding bidirectional perfusion and having a cannula tube to be inserted into a blood vessel of the femoral artery includes a perfusion guide channel formed as a concave part from a predetermined portion of an inner circumferential surface at an end of the cannula tube to an opposite end thereof in a length direction.

In addition, the femoral arterial cannula may further include a through-hole provided at a boundary portion between the perfusion guide channel and the cannula tube, in an end direction of the cannula tube.

In addition, a guide outer wall protruding from an upper end of the through-hole and extending towards the perfusion guide channel may be provided.

In addition, the cannula tube may have a lumen diameter of 5 mm to 8 mm, and the through-hole may have a lumen diameter of 2 mm to 3 mm.

In addition, the perfusion guide channel may have a round furrow shape.

According to another embodiment of the present invention, a cannula having a cannula tube to be inserted into a blood vessel of the femoral artery includes a through-hole provided at a predetermined portion of an inner circumferential surface of an end of the cannula tube and a guide cover provided at an upper portion of the through-hole to cover the upper portion of the through-hole and guide perfusion.

In addition, the guide cover may be slanted with respect to the end of the cannula tube.

In addition, an end of the guide cover may be partially bent inwardly.

In addition, a circumferential surface of the cannula tube positioned outside the femoral artery may be marked to identify a portion at which the perfusion guide channel is positioned or a portion at which the guide cover is positioned.

Advantageous Effects of the Invention

According to a femoral arterial cannula capable of guiding bidirectional perfusion of the present invention, perfusion proceeds towards the distal limb while the femoral arterial cannula is maintained and thus blood may be stably supplied, and, accordingly, ischemia prevalence of the distal limb may be significantly reduced. Thus, the femoral arterial cannula can replace conventional techniques used for distal limb perfusion and thus femoral arterial cannulation may be stably carried out without technical difficulties such as complications or breakage of blood vessels.

In addition, a circumferential surface portion of the cannula at which a guide cover protruding therefrom is positioned has a certain mark outside a blood vessel, and thus the cannula may be taken out by minimizing damage to the blood vessel.

BEST MODE

Hereinafter, exemplary embodiments of a femoral arterial cannula capable of guiding bidirectional perfusion according to the present invention will be described in detail with reference to the accompanying drawings. The present invention should not be construed as being limited by embodiments set forth herein, but may be embodied in many different forms. Rather, these embodiments are provided so that this disclosure will be thorough and complete, and will fully convey the scope of the invention to those skilled in the art.

Figure 1:
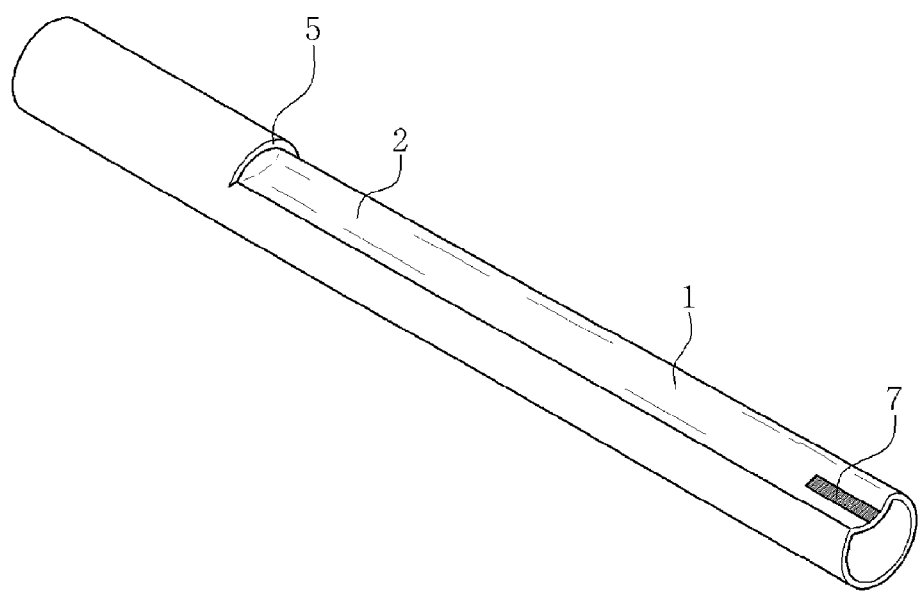
FIG. 1 is a perspective view of an end portion of a femoral arterial cannula capable of guiding bidirectional perfusion according to an embodiment of the present invention.
Figure 2:
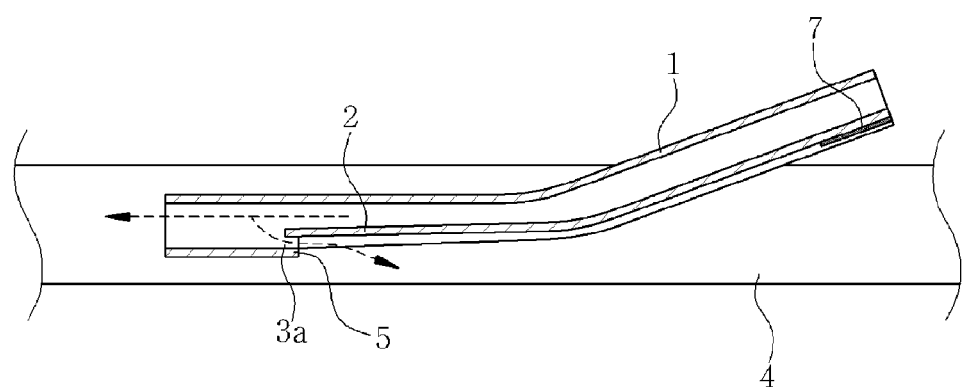
FIG. 2 is a vertical cross-sectional view illustrating a state in which the cannula of FIG. 1 is inserted into the femoral artery.
Figure 3:
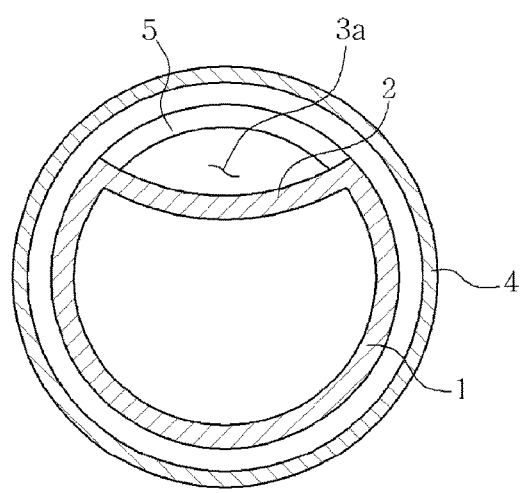
FIG. 3 is a horizontal cross-sectional view illustrating a state in which the cannula of FIG. 1 is inserted into the femoral artery.

FIG. 1 is a perspective view of an end portion of a femoral arterial cannula capable of guiding bidirectional perfusion according to an embodiment of the present invention. FIG. 2 is a vertical cross-sectional view illustrating a state in which the cannula of FIG. 1 is inserted into the femoral artery. FIG. 3 is a horizontal cross-sectional view illustrating a state in which the cannula of FIG. 1 is inserted into the femoral artery.

As illustrated in FIGS. 1 to 3, the femoral arterial cannula capable of guiding bidirectional perfusion according to an embodiment of the present invention is made of a flexible material used in femoral arterial cannulation, and includes a perfusion guide channel 2 and a through-hole 3a provided at an inner side of an end of a cannula tube 1.

The perfusion guide channel 2 is formed as a concave part having a round shape, i.e., a furrow shape, from an inner circumferential surface of the end of the cannula tube 1 to the opposite end thereof in a length direction. As viewed from the horizontal cross-sectional view of FIG. 3, the perfusion guide channel 2 takes a form such that a part of a circumference is inwardly recessed. The cannula of the present invention may include the perfusion guide channel 2 alone. Referring to FIGS. 2 and 3, a part of perfusion proceeding forward at the end of the cannula tube 1 of the cannula of the present invention to be inserted into a blood vessel 4 can inversely flow by the perfusion guide channel 2. That is, a bigger gap between an inner wall of the blood vessel 4 and the perfusion guide channel 2 is formed compared to a case in which the perfusion guide channel 2 is not present, and thus a part of perfusion proceeding forward at the end of the cannula tube 1 may inversely proceed along the perfusion guide channel 2 (see an arrow direction).

The perfusion guide channel 2 is formed by inwardly pressing a part of an inner circumferential surface of the end of the cannula tube 1, and thus form large and small diameter lumens, for example, a larger diameter lumen and a smaller diameter lumen. Accordingly, a vertical step is formed at a boundary portion between the perfusion guide channel 2 and the cannula tube 1 in an end direction of the cannula tube 1, and the through-hole 3a is formed in a vertical plane of the vertical step. Thus, a part of perfusion, proceeding from the inside of the cannula tube 1 of the smaller diameter lumen by the perfusion guide channel 2 towards the cannula tube 1 of the larger diameter lumen of the end thereof, i.e., from the inner side of the cannula tube 1 towards the heart or the lung via the end of the cannula tube 1, flows out in a U-shaped turn at the through-hole 3a. Simultaneously, the part of perfusion flowing out via the through-hole 3a inversely proceeds along the perfusion guide channel 2, thereby supplying blood even to the distal lower extremity, i.e., the distal limb (see an arrow direction).

Meanwhile, as illustrated in FIG. 2, a part of the cannula tube 1 at an upper end of the through-hole 3a may protrude and extend in a direction of the perfusion guide channel 2 to form a guide outer wall 5. The guide outer wall 5 acts as a kind of guide wall to guide a part of perfusion flowing out via the through-hole 3a to stably proceed towards the perfusion guide channel 2 along the guide outer wall 5. Thus, the vertical step may be regarded as the guide outer wall 5 including the through-hole 3a.

The through-hole 3a may have a lumen diameter of about 2 mm to about 3 mm in a cannula generally having a lumen diameter of about 5 mm to about 8 mm, to allow stable perfusion inversion.

When the cannula tube 1 having the above-described structure is inserted into the blood vessel 4 via a blood vessel insertion part, there is no problem because the vertical step formed by the perfusion guide channel 2 is positioned below the blood vessel insertion part. However, when the cannula tube 1 is taken out, the vertical step is caught by a blood vessel wall of the blood vessel insertion part, and thus it is necessary to rotate the cannula tube 1 so that the cannula tube 1 can be taken out of the blood vessel insertion part by positioning the vertical step at the side of the blood vessel insertion part. For this, positions of the perfusion guide channel 2 as well as the vertical step are marked at a predetermined portion of the circumferential surface of the cannula tube 1 positioned outside of the blood vessel 4. Such marks may be formed as marks with colors different from that of the cannula tube 1 or marks having specific shapes, at a portion at which the perfusion guide channel 2 is positioned and at the circumferential surface on the opposite side, respectively, or a mark 7 with a color different from that of the cannula tube 1 or having a specific shape may also be formed only at a circumferential surface of the portion at which the perfusion guide channel 2 is positioned.

MODE OF THE INVENTION

Figure 4:
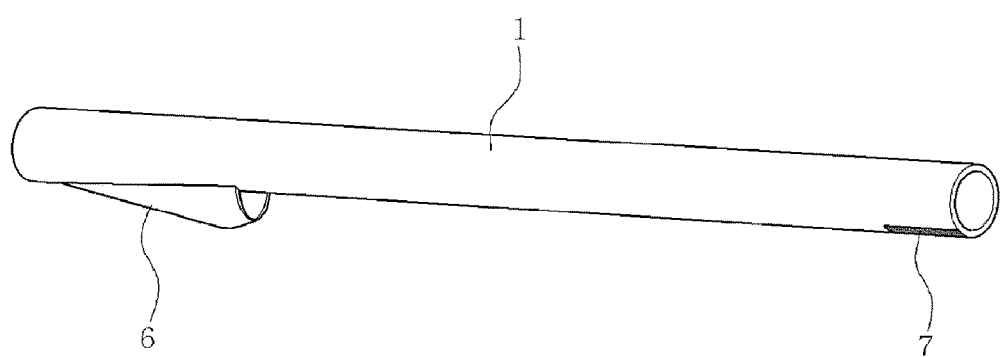
FIG. 4 is a perspective view of a femoral arterial cannula capable of guiding bidirectional perfusion according to another embodiment of the present invention.
Figure 5:
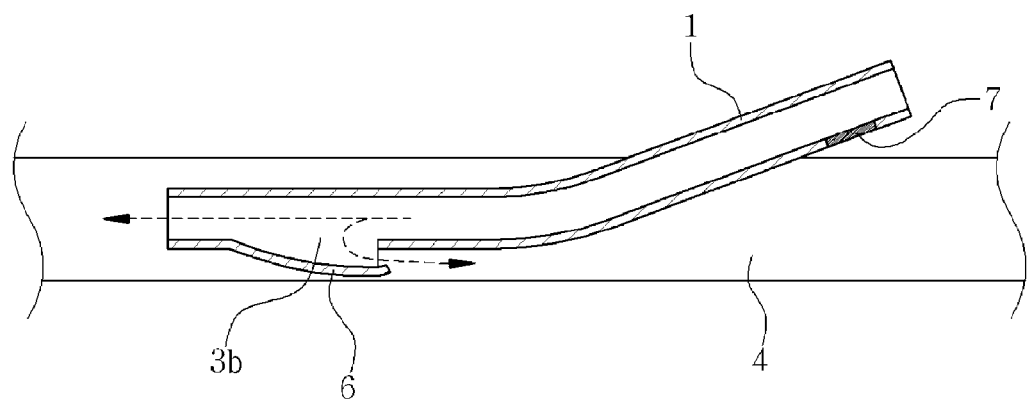
FIG. 5 is a vertical cross-sectional view illustrating a state in which the cannula of FIG. 4 is inserted into the femoral artery.

FIG. 4 is a perspective view of a femoral arterial cannula for perfusion in two directions including a distal direction of the lower extremity of the femoral artery according to another embodiment of the present invention. FIG. 5 is a vertical cross-sectional view illustrating a state in which the cannula of FIG. 4 is inserted into the femoral artery.

As illustrated in FIGS. 4 and 5, the cannula for perfusion in two directions including a distal direction of the lower extremity of the femoral artery according to another embodiment of the present invention is made of a flexible material used in femoral arterial cannulation and includes a through-hole 3b and a guide cover 6 at an inner side of an end of the cannula tube 1.

The through-hole 3b is formed in a part of a circumferential surface of the inner side of the end of the cannula tube 1 to be bigger than the through-hole 3a of the cannula of the aforementioned embodiment, and may be slanted with respect to the opposite end of the cannula tube 1 to perform stable perfusion inversion.

The guide cover 6 protrudes upward from the through-hole 3b by a certain distance therebetween to slantly cover the through-hole 3b, and is slanted with respect to the end of the cannula tube 1 and thus has an opening on the opposite side thereof.

As such, the guide cover 6 is in a slanted form and, accordingly, the cannula tube 1 may be smoothly inserted into the blood vessel 4 via a blood vessel insertion part. In this regard, in a case in which the cannula tube 1 is used after insertion into the blood vessel 4, the guide cover 6 is positioned below the blood vessel insertion part, and thus it is necessary to rotate the cannula tube 1 so that the cannula tube 1 can be taken out via the blood vessel insertion part by positioning the guide cover 6 at the side of the blood vessel insertion part as in the cannula according to the aforementioned embodiment. For this, similarly, a site at which the guide cover 6 is positioned is marked at a predetermined portion of a circumferential surface of the cannula tube 1 positioned outside the blood vessel 4. Such a mark may be formed as a mark with a color different from that of the cannula tube 1 or a mark having a specific shape at the site at which the guide cover 6 is positioned and at the circumferential surface on the opposite side, or a mark 7 with a color different from that of the cannula tube 1 or having a specific shape may be formed only at the circumferential surface of the site at which the guide cover 6 is positioned.

Meanwhile, as described above, when the cannula tube 1 is taken out of the blood vessel through the blood vessel insertion part together with the guide cover 6, as illustrated in FIGS. 4 and 5, an end portion of the guide cover 6 may be slightly bent inwardly to safely take out the cannula tube 1. That is, by slightly bending inwardly the end of the guide cover 6, problems, such as difficulty in taking the cannula tube 1 out because the guide cover 6 is caught by the blood vessel, may be simply addressed.

As in the perfusion guide channel 2 and the through-hole 3a of the aforementioned embodiment, due to the through-hole 3b and the guide cover 6, when blood is supplied via the cannula tube 1 inserted into the blood vessel 4, a part of perfusion, proceeding from the inside of the cannula tube 1 towards the heart or the lung via the end of the cannula tube 1, flows out thereof in a U-shaped turn at the through-hole 3b. Simultaneously, the part of perfusion taken out via the through-hole 3b is guided by the guide cover 6 to inversely proceed, thereby supplying blood even to the distal limb (see an arrow direction).

The cannula tube 1 may be made of a material appropriate for insertion into the body of a patient, for example, a ceramic, a metal, a polymer, or the like. However, a suitable material for the cannula tube 1 may be a type of polymer, which is a flexible plastic material that is biocompatible with organs in the body of a patient and maintains flexibility after insertion into the body of a patient. The polymer material may be, for example, silicone, polycarbonate, urethane mixed with silicone, or polystyrene-polyisobutylene-polystyrene (SIBS).

In addition, inner and outer surfaces of the cannula tube 1 may be coated to form a flexible outer coating to prevent perfusion from flowing through side walls and take blood clotting and coagulation into consideration, and the flexible outer coating may be formed of various materials such as an elastic polymer. In addition, the coating process may be generally performed through immersion in a polymer solution, and non-limiting examples of suitable polymers include: biocompatible polymers, for example, polyvinylchloride, polyolefins (e.g., polyethylene, polypropylene, and an ethylene-vinylacetate copolymer), polyamides, polyesters (e.g., polyethylene terephthalate (PET), and polybutylene terephthalate), polyurethanes, polystyrene resins, fluorine-based resins (e.g., polytetrafluoroethylene and an ethylene-tetrafluoroethylene copolymer), and polyimides; and various elastic polymers, for example, polyurethane-based elastic polymers, polyester-based elastic polymers, polyolefin-based elastic polymers, polyamide-based elastic polymers, silicone rubber, latex rubber, and combinations thereof.

The material or coating of the cannula may prevent a cell or a plaque from growing thereon or being attached thereto.

Although femoral arterial cannulas capable of guiding bidirectional perfusion according to the present invention have been described with reference to the accompanying drawings, the present invention should not be construed as being limited by the embodiments set forth herein and the drawings. In addition, various changes and modifications may be made by those of ordinary skill in the art within the spirt and scope of the present invention.

INDUSTRIAL APPLICABILITY

According to present invention, perfusion proceeds towards the distal limb while a femoral arterial cannula is maintained and thus blood may be stably supplied and, accordingly, the femoral arterial cannula may be usefully used as a femoral arterial cannula capable of guiding bidirectional perfusion that may significantly reduce ischemia prevalence of the distal limb.

Thus, the femoral arterial cannula can replace conventional techniques used for distal limb perfusion and may be usefully used as a femoral arterial cannula capable of guiding bidirectional perfusion that may stably perform femoral arterial cannulation without technical difficulties such as complications or breakage of blood vessels.

In addition, a circumferential surface portion of the cannula, at which a protruding guide cover is positioned, has a certain mark outside a blood vessel, and thus the cannula may be usefully used as a femoral arterial cannula capable of guiding bidirectional perfusion that may take the cannula out by minimizing damage to the blood vessel.

The invention claimed is:
1. A femoral arterial cannula capable of guiding bidirectional perfusion and having a cannula tube to be inserted into a blood vessel of the femoral artery, the femoral arterial cannula comprising
    a perfusion guide channel formed as a concave part from a predetermined portion of an inner circumferential surface at an end of the cannula tube to an opposite end of the cannula tube in a length direction,
    a through-hole provided at a boundary portion between the perfusion guide channel and the cannula tube in an end direction of the cannula tube, wherein the perfusion guide channel is formed by inwardly pressing a part of the inner circumferential surface of the end of the cannula tube.

2. The femoral arterial cannula according to claim 1, wherein a guide outer wall protruding from an upper end of the through-hole and extending towards the perfusion guide channel is formed.

3. The femoral arterial cannula according to claim 1, wherein the cannula tube has a lumen diameter of 5 mm to 8 mm.

4. The femoral arterial cannula according to claim 3, wherein the through-hole has a lumen diameter of 2 mm to 3 mm.

5. The femoral arterial cannula according to claim 1, wherein the perfusion guide channel has a round furrow shape.

6. The femoral arterial cannula according to claim 1, wherein a circumferential surface of the cannula tube is marked to identify a portion at which the perfusion guide channel is positioned.

\* \* \* \* \*